US006485964B1

(12) United States Patent
Wu et al.

(10) Patent No.: US 6,485,964 B1
(45) Date of Patent: *Nov. 26, 2002

(54) TRANSGENIC MAMMALS LACKING EXPRESSION OF ERYTHROPOIETIN OR OF ERYTHROPOIETIN RECEPTOR, TRANSGENIC MAMMALS EXPRESSING CHIMERIC ERYTHROPOIETIN RECEPTORS, CONSTRUCTS FOR PRODUCING THE TRANSGENIC MAMMALS AND USES THEREFOR

(75) Inventors: Hong Wu, Brookline, MA (US); Xin Liu, Brookline, MA (US); Harvey F. Lodish, Brookline, MA (US); Lutz B. Giebel, San Mateo, CA (US); Michael J. Ross, Hillsborough, CA (US); David Matthews, San Francisco, CA (US)

(73) Assignees: Arris Pharmaceutical Corporation, South San Francisco, CA (US); Whitehead Institute for Biomedical Research, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/839,605

(22) Filed: Apr. 15, 1997

Related U.S. Application Data

(63) Continuation of application No. 08/540,366, filed on Oct. 6, 1995, now abandoned, which is a continuation-in-part of application No. 08/467,234, filed on Jun. 6, 1995, now abandoned, which is a continuation-in-part of application No. 08/407,462, filed on Mar. 20, 1995, now abandoned.

(51) Int. Cl.$^7$ .................. C12N 15/00; C12N 15/09; C12N 15/63; C12N 15/70
(52) U.S. Cl. .................. 435/320.1; 536/23.1; 800/18; 800/25
(58) Field of Search .................. 435/69.1, 69.7, 435/172.1, 172.3, 320.1, 325, 455; 930/90; 536/23.5, 23.1; 800/18, 25

(56) References Cited

U.S. PATENT DOCUMENTS 5,278,065 A * 1/1994 D'Andrea et al. ........ 435/252.3

FOREIGN PATENT DOCUMENTS

| WO | 94/28122 | 12/1994 |
|---|---|---|
| WO | 94/29458 | 12/1994 |

OTHER PUBLICATIONS

Wu et al., Proc. Natl. Acad. Sci., USA, 91:2819–2823, 1994.*
McDonald et al., Molecular and Cellular Biology, 6:842–848, 1986.*
Shoemaker et al., Molecular and Cellular Biologoy, 6:849–858, 1986.*
McBurney et al., Nucleic Acids Research, 19:5755–5761, 1991.*
Rudnicki et al., Cell, 71:383–390, 1992.*
Todokoro et al., Mouse gene for erythropoietin receptor, GenBank Accession #X53081, 1992.*
Shoemaker et al., Mouse erythropoietin gene, GenBank Accession #M12482, 1994.*
Mortensen et al., Molecular and Cellular Biology, vol. 12, pp. 2391–2395, May 1992.*
McDonald et al., Molecular and Cellular Biology, vol. 6, pp. 849–858, Mar. 1986.*
Mansour et al., Nature, vol. 336, pp. 348–352, Nov. 24, 1988.*
Wu et al., "Double Replacement: Strategy for efficient introduction of subtle mutations into the murine Colla–1 gene by homologous recombination in embryonic stem cells," Proc. Natl. Acad. Sci. USA, 91:2819–2823 (Mar. 1994).
Shoemaker et al., "Murine erythropoietin gene: cloning, expression, and human gene homology," Mol. Cell. Biol., 6:849–58 (Mar. 1986).
McDonald et al., "Cloning, Sequencing, and Evolutionary Analysis of the Mouse Erythropoietin Gene," Mol. Cell. Biol., 6:842–848 (Mar. 1986).
Pharr et al., "Expression of a constitutively active erythropoietin receptor in primary hematopoietic progenitors abrogates erythropoietin dependence and enhances erythroid colony–forming unit, erythroid burst–forming unit, and granulocyte/macrophage progenitor growth," Proc. Natl. Acad. Sci. USA, 90:938–942 (Feb. 1993).
Youssoufian et al., "Structure, Function, and Activation of the Erythropoietin Receptor," Blood, 81:2223–2236 (May 1993).
D'Andrea et al., "Expression Cloning of the Murine Erythropoietin Receptor," Cell, 57:277–285 (Apr. 1989).
Yamanaka et al. "Targeted disruption of the Hexa gene in mice with biochemical and pathologic features of Tay–Sachs disease." Proc. Natl. Acad. Sci., 91: 9975–9979 (1994).

* cited by examiner

Primary Examiner—Scott D. Priebe
Assistant Examiner—Peter Paras, Jr.
(74) Attorney, Agent, or Firm—Finnegan, Henderson, Farabow, Garrett, & Dunner, LLP

(57) ABSTRACT

Transgenic nonhuman mammals, such as transgenic mice, which lack erythropoietin expression, in which the erythropoietin receptor is deleted, which carry a heterologous erythropoietin receptor (e.g., a chimeric receptor); constructs useful for producing such transgenic nonhuman mammals, embryonic stem cells containing the constructs, a method of producing the transgenic nonhuman mammals and a method of identifying erythropoietin mimics or mimetics.

2 Claims, 2 Drawing Sheets

US 6,485,964 B1

TRANSGENIC MAMMALS LACKING EXPRESSION OF ERYTHROPOIETIN OR OF ERYTHROPOIETIN RECEPTOR, TRANSGENIC MAMMALS EXPRESSING CHIMERIC ERYTHROPOIETIN RECEPTORS, CONSTRUCTS FOR PRODUCING THE TRANSGENIC MAMMALS AND USES THEREFOR

RELATED APPLICATIONS

This application is a file-wrapper-continuation of application Ser. No. 08/540,366 now abandoned, filed Oct. 6, 1995, which is a continuation-in-part of U.S. Ser. No. 08/467,234 now abanonded, filed Jun. 6, 1995, which is a continuation-in-part of U.S. Ser. No. 08/407,462 now abondaned, filed Mar. 20, 1995, by Hong Wu, Xin Lui and Harvey F. Lodish.

BACKGROUND OF THE INVENTION

Erythropoietin (EPO), a 34 kd glycoprotein hormone produced primarily by the kidney, is the principal factor regulating erythropoiesis and plays a key role in stimulating erythrocyte formation in higher organisms. It serves as both mitogen and survival factor which acts on erythroid progenitors, such as erythroid colony-forming units (CFU-E), to promote these cells to proliferate and, possibly, to maturate. EPO is necessary for the replacement of erythrocytes which must occur on an ongoing basis because mature erythrocytes cannot grow or divide and have a limited lifespan. EPO can be used therapeutically for treatment of anemia.

The function of EPO in erythropoiesis is mediated by its cellular receptor (EPOR), a 507 amino acid polypeptide with a single transmembrane domain. Although the EPOR is expressed in a cell type-restricted fashion, i.e., in cells of erythroid lineage, its transcripts have also been etected in non-erythroid cell types such as megakaryocyte, ast cells, umbilical vein endothelial cells and cells with euronal characteristics.

SUMMARY OF THE INVENTION

The present invention relates to transgenic nonhuman ammals and their progeny, such as transgenic mice and their progeny, in which expression of erythropoietin is lacking (e.g., deleted); the endogenous (naturally occurring) erythropoietin receptor is deleted; the endogenous erythropoietin receptor is replaced by a heterologous erythropoietin receptor (i.e., one not present in the corresponding nontransgenic or wild type mammal); erythropoietin expression is lacking and the erythropoietin receptor is deleted; or erythropoietin expression is lacking and the erythropoietin receptor is replaced by a heterologous erythropoietin receptor. Transgenic mammals in which EPO expression is lacking or the EPOR is deleted (i.e., transgenic nonhuman animals carrying null mutations in the Epo gene or EpoR gene) are produced by knocking out (deleting or otherwise disabling) the endogenous EPO gene (Epo) or the endogenous EPO receptor gene (EpoR), respectively, using methods described herein and known to those in the field. Transgenic mammals in which the endogenous EPOR is replaced by a heterologous EPOR can carry a chimeric EPOR, such as a human/mouse chimeric EPOR, or an EPOR of another species, such as the human EPOR present in a mouse. Transgenic mammals in which EPO expression is lacking and the EPOR is lacking or is a heterologous EPOR are produced by breeding mice which lack EPO expression (EPO gene knockout mice) with mice in which, respectively, the EPOR is lacking or is a heterologous EPOR. For example, transgenic mice in which EPO expression is lacking and the mouse EPOR (mEPOR) is replaced with the human EPOR (hEPOR) are produced by breeding mice which are EPO gene knockouts with mice carrying the hEPOR gene. The transgenic mice or other nonhuman transgenic mammal can be heterozygous or homozygous for the knockout or deletion.

A further subject of the present invention is mammalian, nonhuman embryonic stem (ES) cells or cell lines in which the EPO gene or the EPOR gene has been knocked out (deleted or otherwise disabled) by the methods described herein and embryonic stem cell lines in which the EPOR gene has been replaced by a gene encoding a heterologous EPOR, which is a chimeric (e.g., human-mouse) EPOR or an EPOR which is not chimeric and is an EPOR from another animal (e.g., a gene encoding the hEPOR replacing the mEPOR).

The present invention also relates to nucleic acid constructs, particularly DNA constructs, useful for producing the transgenic nonhuman mammals, such as transgenic mice, described herein. It also relates to methods of identifying or designing agents or drugs, such as small molecules, which mimic the effects or activity of EPO. In a method of the present invention, a candidate agent is administered, for example, to a transgenic mouse and the effect of the agent on erythropoiesis is assessed. The transgenic mouse can, for example, lack EPO expression and carry a human/mouse chimeric EPOR in which the extracellular domain is the human EPOR extracellular domain, the transmembrane domain is either the mouse or the human EPOR transmembrane domain and the intracellular domain is the mouse EPOR intracellular domain. If, after the candidate agent is administered to the transgenic animal, the animal displays effects associated with administration of EPO (e.g., enhanced erythropoiesis, treatment of anemia), the agent is EPO-like in its effects; such an agent is referred to as an EPO mimic or EPO mimetic. An agent shown to have EPO-like effects in a transgenic animal in which the EPOR extracellular domain is human is particularly desirable because it has a demonstrated effect on the human EPOR. The present invention further relates to EPO mimics or mimetics and their use. Such EPO mimics can be used prophylactically or therapeutically in any context in which EPO can be used (e.g., to prevent or treat anemia, such as the anemia associated with renal failure).

BRIRF DESCRIPTION OF THE DRAWINGS

DETAILED DESCRIPTION OF THE INVENTION

Definitions

Figure 1:
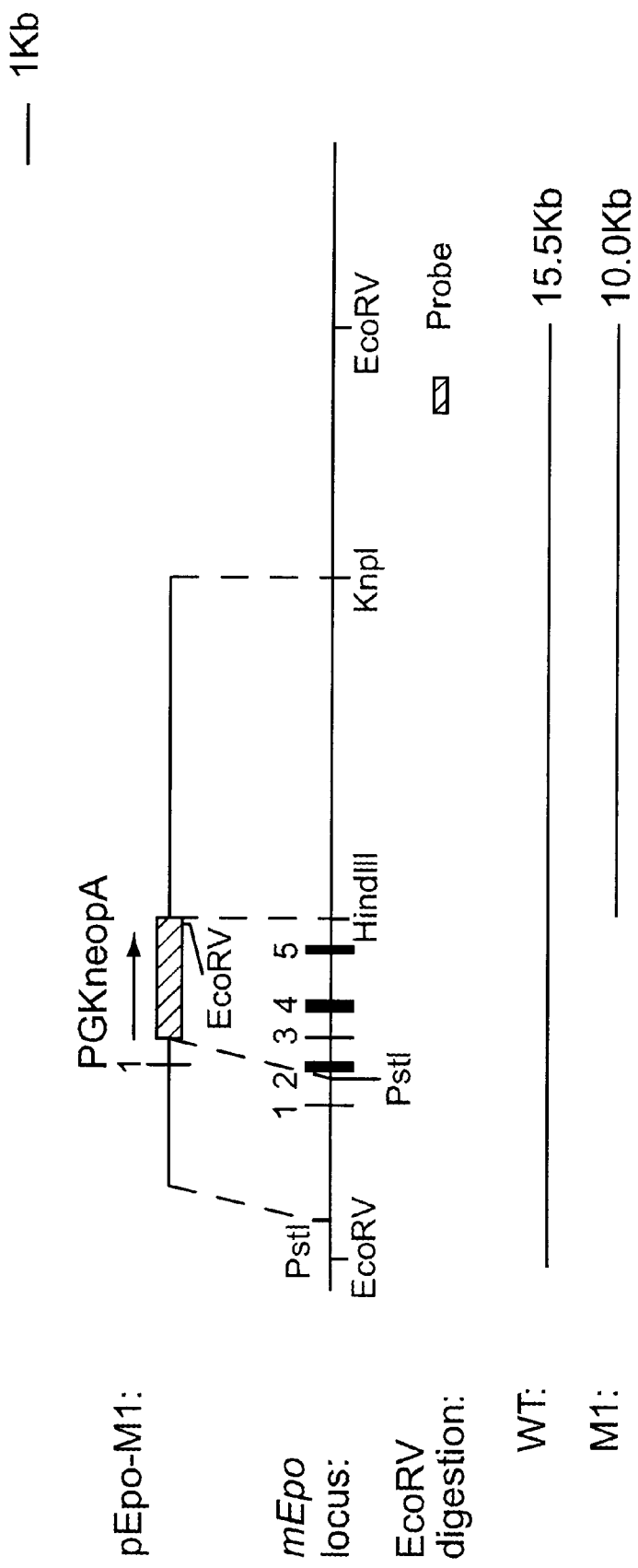
FIG. 1 is a schematic representation of inactivation of the mouse erythropoietin gene (Epo) by homologous recombination in embryonic stem cells.
Figure 2:
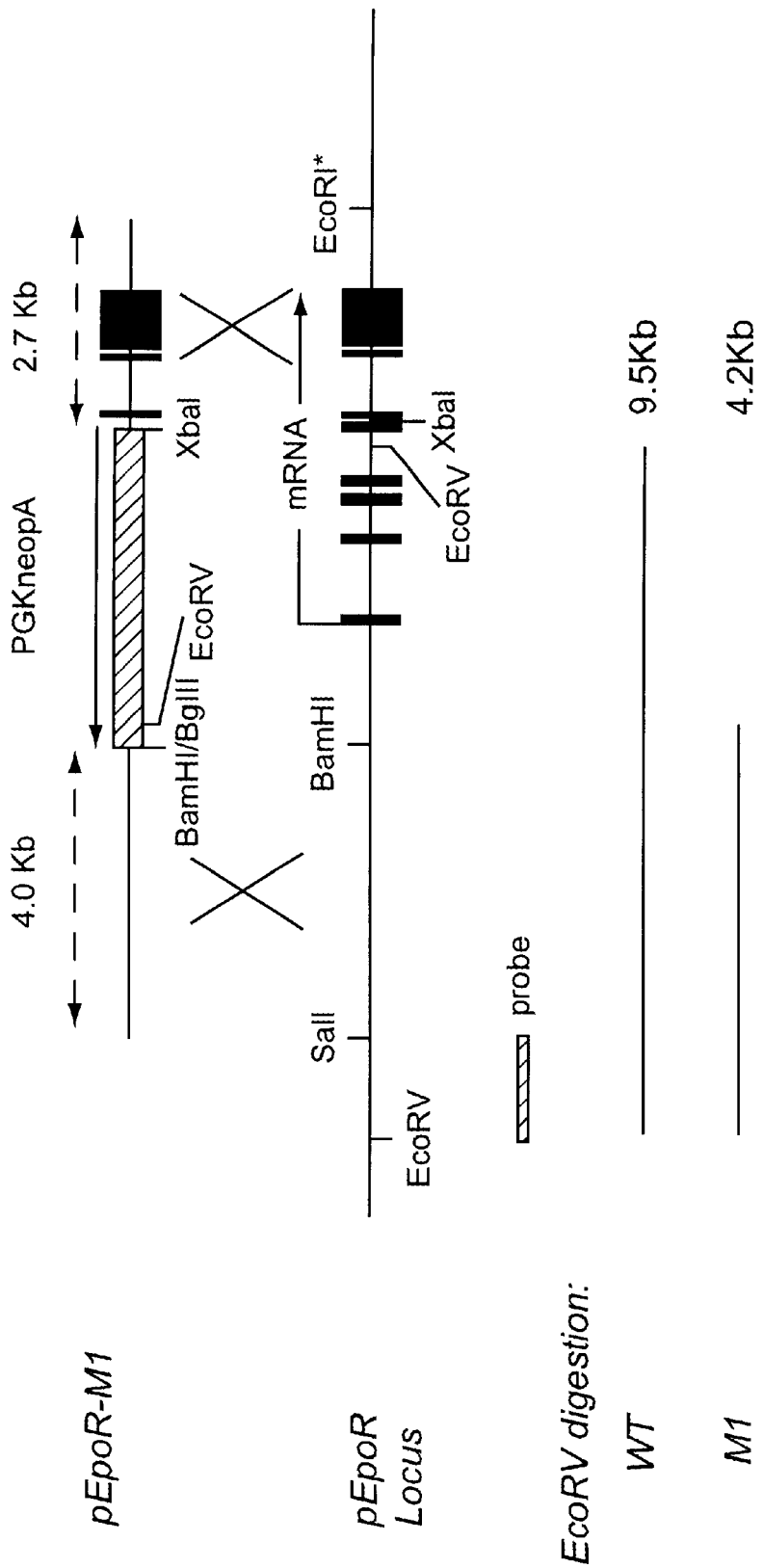
FIG. 2 is a schematic representation of inactivation of the mouse erythropoietin receptor gene (EpoR) by homologous recombination in embryonic stem cells.

Unless otherwise stated, the following terms used in this specification and the claims have the meanings given below:

"Transgenic" means containing genetic material other than that which occurs naturally in a specific nonhuman mammal. "Transgene" means a DNA construct which is introduced into a specific nonhuman mammal.

"Functional transgene" means a transgene which is added to cellular DNA or replaces a specific endogenous gene and is a functional heterologous gene, such as a or chimeric gene or is a regulatory element.

"Progeny" means offspring or succeeding generations thereof.

"Heterozygous" means bearing different alleles at a specified genetic locus.

"Homozygous" means bearing identical alleles at a pecified genetic locus.

"Null mutation" means a mutation which annuls the function of a specified gene.

"Endogenous" means pertaining to material which is natural to a specified nonhuman mammal.

"Heterologous" means pertaining to material which is introduced into or unnatural to a specific nonhuman mammal.

"Chimeric" means pertaining to a combination of materials from different sources, such as a combination of endogenous and heterologous material.

"Erythropoietin mimetic" means a molecule other than natural erythropoietin which mimics the pharmacological activity of natural erythropoietin.

"Nonhuman mammal" means any mammal other than human and includes but is not limited to mouse.

"Transgenic nonhuman mammal" means a nonhuman mammal bearing a transgene and includes the progeny thereof.

"Genetic Material" means any material which can encode for and express protein, including but not limited to genomic DNA, cDNA, degenerate forms of endogenous DNA and combinations thereof.

The present invention relates to transgenic nonhuman mammals in which EPO and/or EPOR expression is lacking. That is, the invention relates to a transgenic nonhuman animal carrying a null mutation in the Epo gene and/or EpoR gene (an EPO or EPOR knockout transgenic nonhuman animal). In one embodiment, the endogenous Epo gene in mice has been knocked out. As described in Examples 1 and 3, an example of a transgenic mouse that carries a null mutation for the Epo gene is a transgenic mouse comprising a first 2.5 Kb PstI-PstI fragment from the 5' end of the murine Epo gene, a second 5.0 Kb HindIII-KpnI fragment from the 3' end of the murine Epo gene and a DNA fragment encoding a selectable marker positioned between the first and second fragments. In a further embodiment, the expression or production of the EPOR gene has been knocked out. As described in Examples 2 and 3, an example of a transgenic mouse that carries a null mutation for the EPOR gene is a transgenic mouse comprising a first 4 Kb SalI-BamHI fragment of the 5' end of mouse EPOR gene, a second 2.7 Kb XbaI-EcoRI fragment from the 3' end of mouse EPOR gene and DNA encoding a selectable marker positioned between the first and second fragments. As used herein, the term "knocked out" refers to deletion of all of an endogenous gene or deletion or alteration of a portion of the endogenous gene with the result that expression or production of the encoded polypeptide is partially or completely suppressed.

A knockout construct is a nucleic acid sequence, such as a DNA construct, which, when introduced into a cell, results in suppression (partial or complete) of expression of a polypeptide or protein encoded by endogenous DNA in the cell. A cell or animal in which expression of a polypeptide is suppressed completely is referred to as a cell or animal in which expression is lacking (a cell or animal carrying a null mutation). The knockout construct is introduced into a cell, such as an ES cell, using known methods such as electroporation. In the ES cell the construct integrates into genomic DNA (e.g., through homologous recombination), resulting in removal or disruption of endogenous DNA, which, as a result, is not transcribed. The resulting ES cell, which now has the targeted gene (e.g., the Epo or EpoR gene) knocked out, is introduced into a developing embryo, with which it integrates.

The present invention also relates to transgenic nonhuman animals in which the EPOR is a heterologous EPOR (an EPOR not present in the corresponding nontransgenic animal). In one embodiment, a transgenic nonhuman mammal carries a functional transgene (i.e., DNA which either encodes a product which alters EPO or EPOR expression, or is itself a sequence which alters EPO or EPOR expression, such as a promoter or enhancer) for a chimeric EPOR comprising genetic material coding for essentially human EPOR extracellular domain. For example, a transgenic nonhuman animal carries a functional transgene for a chimeric EPOR comprising genetic material coding for essentially human EPOR extracellular domain, genetic material coding for essentially human and/or murine EPOR transmembrane domain and genetic material coding for essentially murine EPOR intracellular domain. As described in Examples 3 and 4, an example of a transgenic mouse that carries a functional transgene for chimeric EPOR is a transgenic mouse comprising genetic material essentially equivalent to exons I, VI and VII of murine EpoR gene and genetic material essentially equivalent to exons II, III, IV and V of human EpoR gene. As defined herein, "essentially" as in "essentially human EPOR extracellular domain", "essentially murine EPOR intracellular domain", "genetic material essentially equivalent to exons I and VII of murine EpoR gene" and the like, means that the protein or genetic material referred to is functionally the same as the protein or genetic material endogenous to the identified species. For example, the phrase "essentially human EPOR extracellular domain" refers to any protein, regardless of the kind and/or number of amino acid substitutions or deletions therein, which retains the pharmacological characteristics of human EPOR extracellular domain. Similarly, the phrase "genetic material essentially equivalent to exons I and VII of murine EpoR gene" refers to genetic materials that codes for a protein that is functionally the same as the protein expressed by endogenous murine exons I and VII.

In a second embodiment, the transgenic nonhuman animal carries a functional transgene for an EPOR in which the entire EPOR is an EPOR present in another animal (e.g., another strain of mouse; human).

In a particular embodiment the transgenic nonhuman mammal carries a functional transgene for EPO under the control of a promoter/enhancer system and a functional transgene for a heterologous EPOR (e.g., comprising genetic material coding for essentially human EPOR extracellular domain). For example, such a transgenic mouse bears a functional transgene for EPO under the control of a tetracycline promoter/enhancer system (Khün, R., et al., *Science*, 265:1427–1429 (1995)) and a functional transgene for a chimeric EPOR comprising genetic material coding for essentially human EPOR extracellular domain, genetic material coding for essentially human and/or murine EPOR transmembrane domain and genetic material coding for essentially murine EPOR intracellular domain. In a particular embodiment, a transgenic mouse carries a functional transgene for EPO under the control of a tetracycline promoter/enhancer system and a functional transgene for a chimeric EpoR gene and genetic material essentially equivalent to exons II, III, IV and V of human EpoR gene.

A replacement construct is a nucleic acid sequence, such as a DNA construct, which comprises DNA-encoding a functional heterologous EPOR (a functional transgene) and, when introduced into a cell, such as an ES cell, integrates into genomic DNA and is expressed, resulting in production of the heterologous EPOR. A replacement construct comprises transcriptional and processing elements which allow expression of the encoded heterologous EPOR in cells of the transgenic mammal. For example, a replacement construct is typically comprised of DNA from some portion of the gene (exon sequence, intron sequence and/or promoter sequence) to be suppressed and a marker sequence used to detect the presence of the construct in the cell. The ES cell containing the replacement construct is introduced into a developing embryo, with which it integrates.

Genomic constructs containing DNA which when introduced into cells results in a null mutation for EPO or EPOR (knockout constructs) can be prepared by producing DNA which encompasses the 5' end promoter region of the Epo gene or EpoR gene, the 3' end untranscribed region of the Epo gene or the EpoR gene and a selectable marker. In addition, the construct has additional components necessary and sufficient for expression of the encoded products in the cell. For example, a genomic construct can be prepared by (1) isolating a first DNA fragment encompassing the 5' end promoter region of the Epo gene or EpoR gene, respectively and introducing the fragment into a suitable vector, (2) isolating a fragment of DNA encoding for a selectable marker and inserting the marker adjacent to the first fragment and (3) isolating a second DNA fragment encompassing the 3' end untranscribed region of the Epo gene or EpoR gene and inserting the second fragment adjacent to DNA encoding a selectable marker. Alternatively, the null mutation constructs can be constructed by introducing the DNA segments of the gene into a vector which contains the selectable marker. The DNA fragments encompassing the 3' and 5' end fragments may vary, but must be of sufficient size to effect homologous recombination to the endogenous gene. Alternatively, DNA constructs containing null mutations for Epo and EpoR genes can be prepared by cloning a fragment of DNA encompassing the entire Epo gene or EpoR gene, respectively, into a suitable vector and then introducing a selectable marker in the transcriptional region of the gene.

The cloning procedures can be carried out by methods known to those of ordinary skill in the art. The DNA fragments derived from 3' and 5' end regions of the Epo gene can be obtained from a restriction map generated by Southern blot analysis of genomic DNA clones corresponding to the Epo locus with probes derived from 5' end promoter and 3' end untranslated regions of EPOR cDNA. In a similar fashion, the DNA fragments derived from 3' and 5' end regions of the EpoR gene can be obtained from genomic DNA clones corresponding to the EpoR locus.

Suitable selectable markers include, but are not limited to, neomycin, puromycin and hygromycin. A preferred selectable marker is the PGK-neo gene, which confers resistance to the antibiotic G418. A preferred PGK-neo gene is derived from the plasmid pGEM7(KJ1)R, which contains a PGK-neo gene derived from plasmid pKJ1 and modified by replacing the mutant coding region of neo with wild-type neo sequences by swapping the Eagl-Ncol fragments between pKJ1 and pSV$_2$-neo. Suitable vectors include, but are not limited to, Bluescript, pBR322, pGEM7, preferably Bluescript. Details for preparing the constructs for Epo and EpoR null mutations are provided in the Examples.

Genomic constructs containing a functional transgene for an EPOR (replacement construct) can be prepared in a variety of ways. For example, a replacement construct can comprise genetic material encoding human EPOR extracellular domain can be prepared by cloning a first chimeric construct comprising genetic material essentially equivalent to exons II, III, IV and V, and optionally exons I and VI, of human EpoR gene and introns from murine EpoR gene into a vector containing a construct comprising the exons and introns of murine EpoR gene to produce a second chimeric construct comprising genetic material essentially equivalent to exons I and VI of murine and/or human EpoR gene, exons II, III, IV and V of human EpoR gene and introns and exon VII, VIII of murine EpoR gene. The second chimeric construct is then subcloned into a vector containing a genomic construct of the murine EpoR gene. Exon I of the EPOR codes for the first 13 amino acids of the extracellular domain. Of these 13 amino acids, only residues 2 and 4 differ between the murine and human sequences. Accordingly, genetic material that is essentially equivalent to murine exon I can be used in the human/mouse chimeric constructs of this invention. The cloning and subcloning procedures are preformed by methods known to those of ordinary skill in the art.

The chimeric construct comprising genetic material essentially equivalent to exons II, III, IV and V and optionally exons I and VI of human EpoR gene and introns from murine EPOR can be prepared by ligating together in the appropriate sequence, a number of chimeric DNA fragments which each comprise one or more of the desired human exons and appropriate murine introns. The ligation can be effected by methods known to those of ordinary skill in the art.

For example, suitable chimeric DNA fragments are prepared by "sticky feet" PCR mutagenesis (Clackson, et al., *PCR: A Practical Approach* M. J. McPherson, P. Quirke and G. R. Taylor, eds. IRL Press, Washington, D.C.). The method is carried out by first amplifying exons from human genetic material (cDNA or genomic DNA) using PCR primers comprised of the 5' and 3' ends of human exons and attendant region of the native murine intron to give exons with regions of the native murine intron region at either end to serve as the "sticky feet". The amplified exons are then used as double-stranded mutagenesis primers which are annealed separately or together to template DNA in a site-directed mutagenesis reaction. (See Example 3).

In an alternative method, suitable chimeric DNA fragments can be prepared by oligonucleotide directed mutagenesis, which is carried out using synthetic single-stranded DNA molecules designed to direct the mutation of murine codons to human codons in the exons and performing a series of oligonucleotide-directed mutagenesis reactions to change the desired endogenous exons to their human analogs. Alternatively, suitable chimeric DNA fragments can be prepared by PCR assembly, by amplifying exons from human genetic material (cDNA or genomic DNA) and murine introns from murine genomic DNA using synthetic oligonucleotides designed such that there is some overlap at the intron/exon boundaries and then splicing the PCR products together by combining them in subsequent PCR reactions.

Genomic DNA clones corresponding to the Epo or EpoR locus can be isolated by methods known to those of ordinary skill in the art. For example, murine genomic clones corresponding to the Epo or EpoR locus can be isolated by screening a 129 (J1) genomic library (Wu, H., et al., *Proc. Natl. Acad. Sci., USA*, 91:2519–2823 (1994)) with $^{32}$p-labelled murine EPO or EPOR cDNA fragments. Genomic DNA can be prepared from positive clones according to standard methods (e.g., Sambrook, et al., *Molec. Cloning: A Laboratory manual* 1:2.60–2.80 (1989)).

The ES cells carrying the knockout or replacement construct are introduced into embryos using known methods. For example, they are microinjected into eggs according to methods described by Li et al. and Bradley. (Li, E. et al., Cell, 69:915–926 (1992); Bradley, A., *Teratocarcinomas and Embryonic Stem Cells: A Practical Approach*, E. J. Robertson (ed.), Oxford IRL Press, pp. 113–151 (1987)) The resulting developing embryo (carrying the knockout construct, the replacement construct or both constructs) is introduced (implanted) into an appropriate female and allowed to develop into offspring. Prior to introduction into the female, the resulting embryo can, optionally, be incubated in vitro. The nonhuman mammal which develops from the embryo into which the embryonic stem cell has been introduced is a transgenic nonhuman mammal in which EPO expression is suppressed, the EPOR is not present, a chimeric EPOR or an EPOR of another species has replaced the endogenous EPOR or EPO expression is suppressed and a chimeric EPOR or EPOR of another species is present. The term "transgenic nonhuman mammal" as used herein includes the mammal which develops from the embryo into which the embryonic stem cell was introduced and its progeny (all future generations derived or descending from a particular mammal which contains a knockout construct or a replacement construct in its genomic DNA).

As described herein, targeting vectors or constructs have been produced and used to knock out a mammalian Epo gene and a mammalian EpoR gene. Specifically, knockout constructs were produced and introduced into mouse ES cells by electroporation, resulting in knockout of the endogenous mouse EPO (mEPO) gene and the mouse EPOR (mEPOR) gene. Constructs can also be introduced by other means, such as microinjection. Positive clones (ES cells in which the Epo gene or the EpoR gene is knocked out) were identified and injected into mouse embryos, which were introduced into an appropriate female, in which they developed into offspring. Chimeric mice were backcrossed to nonchimeric mice and germline transmission of the mutant allele was detected. As described in the examples, the mutant allele was transmitted to the germ line as a result of some of the crosses. The positive mice (heterozygous for the deletion) were crossbred to generate homozygotes. Homozygosity for the EPO deletion or the EPOR deletion was lethal. Homozygous animals can be kept alive by, for example, administering EPO or a blood substitute. Alternatively, animals can be maintained as heterozygotes and then crossbred to produce homozygous animals for the assays.

In one embodiment of the present invention, the transgenic nonhuman mammal carries a chimeric (e.g., human/mouse) EPOR in place of the endogenous (e.g., mouse) EPOR. In this embodiment, the chimeric EPOR can be produced by transfecting ES cells carrying the mEPOR knockout with a construct comprising DNA encoding the chimeric EPOR and DNA homologous to endogenous sequences. The construct DNA encoding the chimeric EPOR is introduced into the endogenous DNA, preferably at the location at which the mEPOR would have occurred (i.e., if it had not been knocked out). In one embodiment, the chimeric EPOR. includes a human EPOR extracellular domain, a mouse EPOR transmembrane domain, and a mouse EPOR intracellular domain. Alternatively, the transmembrane domain can be a mammalian transmembrane domain such as the human EPOR transmembrane domain. Further, the transmembrane domain can be a chimeric domain in which both mouse and human portions of the transmembrane domain of the EPO receptor are present. ES cells containing the construct encoding the chimeric EPOR are introduced into embryos, using known methods (e.g., electroporation, microinjection). The resulting embryos containing the constructs are introduced into an appropriate female and allowed to develop to term. The resulting offspring carry the chimeric EPOR and can be bred to produce animals homozygous for the chimeric EPOR. Alternatively, they can be bred with animals which are Epo gene knockouts, to produce progeny which are heterozygous or homozygous for the chimeric EPOR and heterozygous or homozygous for deletion of the Epo gene.

In a further embodiment, the entire endogenous EPOR can be replaced by an EPOR from a different type of animal (e.g., the mEPOR can be replaced by the hEPOR). In this case, the resulting EPOR is not chimeric, but an EPOR from another animal. The replacement EPOR can be an EPOR present in a type of animal other than that of the transgenic animal or can be an EPOR not known to occur in nature and designed in such a manner that it functions as an EPOR and, optionally, has enhanced binding affinity or other additional advantageous characteristics.

Transgenic mammals from any species of rodent, including without limitation, rabbits, rats, hamsters, and mice, can be produced, as can other nonhuman transgenic mammals, such as dog, cat, pig, sheep, cow, and primates. In most cases, the embryonic stem cells (ES cells) used to produce the transgenic mammal will be of the same species as the transgenic mammal to be generated. Thus, for example, mouse embryonic stem cells will usually be used for generation of knockout mice. Transgenic mammals can be prepared using methods known to those of skill in the art. See, for example, Hogan et al. (Ed.), *Manipulating the Mouse Embryo: A Laboratory Manual*, Cold Spring Harbor Laboratory Press, Cold Spring Harbor, N.Y. (1986).

Embryonic stem cells are typically selected for their ability to integrate into and become part of the germ line of a developing embryo so as to create germ line transmission of the knockout construct. Thus, any ES cell line that can do so is suitable for use herein. For example, the J1 ES cell line described in the Examples can be used. Alternatively, suitable cell lines which can be used include, but are not limited to, the 129J ES or the murine stem cell line D3 (American Type Culture Collection catalog no. CRL 1934). The cells are cultured and prepared for DNA insertion using methods well known to the skilled artisan, such as those set forth by Robertson (in: *Teratocarcinomas and Embryonic Stem Cells: A Practical Approach*, E. J. Robertson, ed. IRL Press, Washington,. D.C. [1987]) and by Bradley et al. (*Current Topics in Devel. Biol.*, 20:357–371 [1986]) and by Hogan et al. (Manipulating the Mouse Embryo: *A Laboratory Manual*, Cold Spring Harbor Laboratory Press, Cold Spring Harbor, N.Y. [1986]).

Insertion of the knockout construct or the replacement construct into the ES cells can be accomplished using a variety of methods well known in the art, including, for example, electroporation, microinjection, and calcium phosphate treatment. A preferred method of insertion is electroporation. For insertion of the DNA sequence, the knockout construct DNA or replacement construct DNA is added to the ES cells under appropriate conditions for the insertion method chosen. If the cells are to be electroporated, the ES cells and construct DNA are exposed to an electric pulse using an electroporation machine (electroporator) and following the manufacturer's guidelines for use. After electroporation, the cells are allowed to recover under suitable incubation conditions. The cells are then screened for the presence of the knockout construct or the replacement construct.

Each knockout construct DNA or replacement construct DNA to be inserted into the cell is first typically linearized if the knockout construct has been inserted into a vector. Linearization is accomplished by digesting the DNA with a suitable restriction endonuclease selected to cut only within the vector sequence and not within the knockout construct sequence.

Screening for cells which contain the knockout construct or replacement construct (homologous recombinants) can be done using a variety of methods. For example, as described herein, cells can be processed as needed to render DNA in them available for hybridization with a nucleic acid probe designed to hybridize only to cells containing the construct. For example, cellular DNA can be probed with $^{32}$p labelled DNA which locates outside the targeting fragment. This technique can be used to identify those cells with proper integration of the knockout construct or the replacement construct. The DNA can be extracted from the cells using standard methods, such as those described by Sambrook, J. et al., *Molecular Cloning: A Laboratory Manual*, Second Edition, Cold Spring Harbor Laboratory Press, Cold Spring Harbor, N.Y. (1989). The DNA can then be probed on a Southern blot with a probe or probes designed to hybridize in a specific pattern to genomic DNA digested with (a) particular restriction enzyme(s).

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3–4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2–3 days pseudopregnant females are appropriate.

Germline transmission of the mutant allele can be determined using standard methods. Offspring resulting from implantation of embryos containing the ES cells described above are screened for the presence of the desired alteration (e.g., EPO knockout, EPOR knockout, heterologous EPOR). This can be done, for example, on the basis of coat color, if a coat color selection strategy is used. Alternatively, DNA obtained from offspring (e.g., tail DNA) can be assessed for the knockout construct, using known methods (e.g., Southern analysis, dot blot analysis, PCR analysis). See, For example, Sambrook, J. et al., *Molecular Cloning: A Laboratory Manual*, Second Edition, Cold Spring Harbor Laboratory Press, Cold Spring Harbor, N.Y. (1989). Transgene expression can also be assessed (e.g., to determine if a replacement construct is expressed) by known methods, such as Northern analysis or PCR analysis, to detect transgene in RNA levels. Offspring identified as mosaics can be crossed with one another to produce homozygous knockout animals. As described in the Examples, homozygosity for the Epo gene knockout is lethal. Animals homozygous for the Epo gene deletion (i.e., animals carrying a null mutation in the Epo gene) can be kept alive during development by administration of mouse EPO in utero and by subcutaneous administration of EPO after birth. Alternatively, animals homozygous for the EpoR gene deletion can be maintained through administration of a blood substitute. It is also possible to produce transgenic mice which carry the human/mouse EPOR replacement and the mouse Epo gene (and, thus, mouse EPO, which triggers the human EPOR). This would maintain the mouse, which can be made anemic when needed, such as by treatment in a hyperbaric chamber. High oxygen pressure will turn off EPO production and the mouse will become anemic. The resulting anemic mouse is useful for the assay described herein.

In an alternative embodiment, animals homozygous for a null mutation in the Epo gene and a functional chimeric transgene for EpoR are kept alive through development by the exogenous EPO transgene and after birth by tetracycline-induced deletion of exogenous EPO transgene. While tetracycline also is known to inhibit ribosome synthesis, analogs of tetracycline are available which do not have such properties.

DNA constructs for a functional transgene for EPO under the control of a tetracycline promoter/enhancer system can be prepared by inserting Loxp fragments (Kühn, R., et al., *Science*, 269:1427–1429 (1995)) in front of the murine EPO cDNA and generating transgenic mice according to standard methods (Sambrook, et al., *Molec. Cloning: A Laboratory Manual* 1:2.60–280).

Transgenic mammals (e.g., transgenic mice) of the present invention are useful to identify agents (e.g., small organic molecules, nucleic acids, peptides) which are active in stimulating human EPO receptor and agents which are EPO-like in their activity (e.g., agents which regulate erythropoiesis and stimulate erythrocyte formation), and particularly to identify agents which mimic human EPO (EPO mimetics). They can also be used to identify artificial blood substitutes. In one embodiment, an agent that is active in stimulating human EPO receptor can be identified by administering a test compound or candidate agent to a transgenic mammal (e.g., mouse) which carries an EPO receptor with a human extracellular domain. If the agent stimulates production of red blood cells, then the agent is active in stimulating human EPO receptor. In another embodiment, an EPO mimic or mimetic can be identified by administering a candidate agent to a transgenic mammal which carries an EPO receptor or to a transgenic mouse or other mammal which is an EPO knockout carrying a human/mouse EPOR in which the EPOR extracellular domain is human. If the agent stimulates erythropoiesis in the animal (e.g., as evidenced by increased erythrocyte number), it is an EPO mimic or mimetic and, particularly, a hEPO mimic or mimetic. Alternatively, an EPO knockout mouse in which the EPOR is the mEPOR can be used for the assay. An agent identified by this means can be further tested to assess its ability to bind the hEPOR.

In one embodiment, the method for identifying agents capable of stimulating EPORs to promote erythropoiesis comprises (A) administering a test agent to a transgenic mouse homozygous for a functional transgene comprising genetic material coding for essentially human EPOR extracellular domain; and (B) measuring the erythropoietic effect of the test agent. In addition, the transgene can comprise genetic material coding for essentially human EPOR extracellular domain, genetic material coding for essentially human and/or murine EPOR transmembrane domain and any genetic material coding for essentially murine EPOR intracellular domain. Further, the transgene can comprise any genetic material essentially equivalent to exons I, VI and VII of murine EpoR gene and any genetic material essentially equivalent to exons II, III, IV and V of human EpoR gene.

In another embodiment, the method for identifying agents capable of simulating EPORs to promote erythropoiesis comprises (A) administering a test agent to a transgenic mouse homozygous for a null EPO mutation and homozygous for a functional transgene comprising any genetic material coding for essentially human EPOR extracellular domain; and (B) measuring the erythropoietic effect of the test agent. In addition, the null transgene mutation can comprise a first 2.5 Kb PstI-PstI fragment of the 5' end of the murine Epo gene, a second 5 Kb HindIII-KpnI fragment of the murine Epo gene and a DNA fragment encoding a selectable marker positioned between the first and second fragments, and the functional transgene comprises genetic material coding for essentially human EPOR extracellular domain, genetic material coding for essentially human and/or urine EPOR transmembrane domain and any genetic material coding for essentially murine EPOR intracellular domain. Further, the functional transgene comprises any genetic material essentially equivalent to exons I, VI and VII of murine EpoR gene and genetic material essentially equivalent to exons II, III, IV and V of human EpoR gene.

In another embodiment, the method for identifying agents capable of stimulating EPOR to promote erythropoiesis comprises (A) administering a test agent to a transgenic mouse homozygous for a functional transgene for EPO under the control of a tetracycline promoter/enhancer system and homozygous for a functional transgene for EPOR comprising genetic material coding for essentially human EPOR extracellular domain; and (B) measuring the erythropoietic effects of the test agent.

In another embodiment, the method for identifying agents capable of stimulating EPORs to promote erythropoiesis comprises (A) administering a test agent to a transgenic mouse homozygous for a functional transgene for EPO under the control of the above-described promoter/enhancer system and homozygous for a functional transgene for EPOR comprising any genetic material coding for essentially human EPOR extracellular domain, any genetic material coding for essentially human and/or murine EPOR transmembrane domain and any genetic material coding for essentially murine EPOR intracellular domain. Further, the functional transgene for EPOR can comprise any genetic material essentially equivalent to exons I, VI and VII of murine EpoR gene and any genetic material essentially equivalent to exons II, III, IV and V of human EpoR gene.

The EPO receptor in the methods of the present invention can be a complete human EPO receptor or a chimeric receptor. For example, the EPO receptor can have a mouse or human intracellular domain. Further, the EPO receptor can have a mouse transmembrane domain, a human transmembrane domain, or a chimeric transmembrane domain (e.g., a transmembrane domain which includes both mouse and human portions of the EPO receptor transmembrane domain).

In addition, in the methods of the present invention, a transgenic mammal (e.g., mouse) can be used which produces EPO or does not produce EPO. In the method in which the transgenic mammal produces EPO, the methods of the present invention can further comprise maintaining the transgenic mammal under high-oxygen conditions sufficient to depress EPO production, reducing oxygen availability and then administering the test compound or agent. A transgenic mammal which does not produce EPO can be a transgenic mammal missing genetic information encoding mouse EPO receptor. For example, an EPO knockout mouse, which is homozygous for EPO knockout or an EPO knockout mouse which is a cross-bred mouse in which one ancestral line is heterozygous for mouse EPO knockout and one ancestral line is heterozygous for the EPO receptor, can be used in the methods of the present invention. Further, the transgenic mammal used in the assays of the present invention can be heterozygous for the EPO receptor and for mouse EPO receptor production, or homozygous for EPO receptor production.

The present invention will now be illustrated by the following Examples, which are not intended to be limiting in any way.

EXAMPLES

Example 1

Construction of Targeting Vector for EPO Knock Out

Genomic DNA clones corresponding to the Epo locus were isolated from a 129(J1) genomic library (Wu, H. et al., Proc. Natl. Acad. Sci., USA, 91:2819–2823 (1994)). A restriction map was generated by Southern blot analysis with probes derived from the EPO cDNA, the 5' end promoter region and the 3' end untranscribed region. Targeting vector pEPO-M1 was constructed by first inserting the 2.5 Kb PstI-PstI fragment from the 5' end of the Epo locus (gene) into a Bluescript vector, forming pEPO-M1-5'. Then a 1.8 Kb EcoRI-HindIII fragment from the plasmid pGEM7 (KJ1)R (Rudnicki, M. A. et al., Cell, 71:383–390 (1992)) containing PGKneopA sequences was inserted into the coRI and HindIII sites of the pEPO-M1-5' vector forming EPO-M1-neo) Finally, a 5.0 Kb HindIII-KpnI fragment from the 3' region of the Epo gene was inserted into the HindIII and KpnI sites of the pEPO-M1-neo vector.

Electroporation, Isolation of ES Clones and Southern Analysis

J1 ES cells were cultured essentially as described (Li, E. et al., Cell, 69:915–926 (1992)). To introduce the targeting vector into the endogenous Epo gene, 25 µg of pEPO-M1 plasmid was linearized at the NotI site of the vector sequence and electroporated into $1 \times 10_7$ J1 ES cells in a volume of 0.8 ml at 400V and 25 µF by use of Bio-Rad Gene Pulser. After 24 hours of culture, the ES medium was supplemented with 400 µg/ml of G418 (GIBCO/BRL) and 400 ES clones were isolated after 7–10 days of selection. Individual clones were expanded, and genomic DNAs were prepared as described (Laird, P. W. et al., Nucleic Acids Res., 19:4293 (1991)). DNAs were digested with EcoRV and resolved on a 0.7% agarose gel. After transferring, filters were hybridized with $^{32}P$ labeled 1.7 Kb HindIII fragment which locates outside of the targeting vector. A 10.0 Kb band corresponding to the targeting allele was detected in 10.8% of ES clones isolated.

The murine Epo gene is encoded by five exons within 2.7 kb of genomic DNA (McDonald et al., 1986; Shoemaker and Mitsock, 1986). The translational start site (ATG) is located in the first exon. A replacement-type targeting vector, pEpo-M1, that contains 2.5 kb upstream and 5.0 kb downstream flanking sequences of the Epo gene, and the PGKneopA cassette for positive selection was constructed. Exons 2–5 were completely deleted so that no EPO protein could be produced from the mutant allele. After electroporation and drug selection, G418-resistant (G418') clones from embryonic stem (ES) cells were isolated. DNAs from individual clones were prepared and digested with EcoRV. After gel separation, filters were hybridized with an external probe from the 3' flanking region. A 10.0 kb band corresponding to the targeted allele was detected in 10.8% of ES clones isolated.

Example 2

Construction of Targeting Vector for EPOR Knock Out

Genomic DNA clones corresponding to the EpoR locus were isolated from a 129 (J1) genomic library (Wu, H. et al., Proc. Natl. Acad. Sci., USA, 91:2819–2823 (1994)). A restriction map was generated by Southern blot analysis with probes derived from the EPOR cDNA, the 5' end promoter region and the 3' end untranscribed region. Targeting vector pEPOR-M1 was constructed by first replacing a BglII-BamHI fragment in the plasmid pGEM7(KJ1)R (Rudnicki, M. A. et al., *Cell*, 71:383–390 (1992)) with a 4 Kb SalI-BamHI fragment derived from the 5' end of the EpoR locus, yielding pEpoR-M1-5', and then inserting 2.7 Kb XbaI-EcoRI* (site in the polylinker) fragment derived from the 3' end of the EpoR gene into the XbaI and EcoRI sites of the plasmid pEpoR-M1–5'.

Electroporation, Isolation of ES clones and Southern Analysis J1 ES cells were cultured essentially as described (Li, E. et al., *Cell*, 69:915–926 (1992)). To introduce the targeting vector into the endogenous EpoR gene, 25 µg of pEPOR-M1 plasmid was linearized at the SalI site, and electroporated into $1 \times 10^7$ J1 ES cells in a volume of 0.8 ml at 400V and 25 µF by use of a Bio-Rad Gene Pulser. After 24 hours of culture, the ES medium was supplemented with 400 µg/ml of G418 (GIBCO/BRL), and 400 ES clones were isolated after 7–10 days of selection. Individual clones were expanded, and genomic DNAs were prepared as described (Laird, P. W. et al., *Nucleic Acids Res.*, 19:4293 (1991)). DNAs were digested with EcoRV and resolved on a 0.7% agarose gel. After transferring, filters were hybridized with $^{32}$P labeled 1 Kb EcoRV-SalI fragment which locates outside of the targeting vector. A 4.2 Kb band corresponding to the targeting allele was detected in 13.5% of ES clones isolated.

The EpoR gene is encoded by eight exons with the transmembrane domain encoded by exon 6. The minimum promoter is located 0.5 kb upstream of the transcription initiation site (Youssouflan et al., 1993). To silence the EpoR gene completely, the EpoR-M-1 plasmid, in which a 4.7 kb BamHI-XbaI fragment from the EpoR locus, including 1.6 kb from the 5' flanking region and exons 1–6, was deleted and replaced with PGKneopA for position selection. Among 400 G418' ES clones isolated, homologous recombination occurred at a frequency of 13.5%.

Example 3
Generation of Germline Chimeras

Five lines of positive ES clones containing the EPO null mutation were injected into Balb/c or C57BL/6 embryos. Chimeric mice were backcrossed to Balb/c or C57BL/6 mice, and germline transmission of the mutant allele was detected by Southern blot analysis of tail DNA from F1 offspring with agouti coat color. Four lines have transmitted the mutant allele to the germ line.

Six lines of positive ES clones containing the EPOR null mutation were injected into Balb/c or C57BL/6 embryos. Chimeric mice were backcrossed to Balb/c or C57BL/6 mice, and germline transmission of the mutant allele was detected 30 by Southern blot analysis of tail DNA from F1 offspring with agouti coat color. Two lines have transmitted the mutant allele to the germ line.

Epo$^{-/-}$ and EpoR$^{-/-}$ Mice Are Embryonic Lethal

Targeted ES clones carrying null mutations in the Epo or EpoR genes were injected into C57BL/6 or BALB/c blastocysts, and the resulting chimeric mice were backcrossed. Germline transmission of the mutant allele was detected by Southern blot analysis of tail DNA from F1 offspring. Four and two independently isolated ES clones transmitted the mutant Epo and EpoR alleles, respectively, to the germline.

Heterozygotes carrying deletions in either the Epo or EpoR genes appeared normal and were viable and fertile. The levels of blood hemoglobin, hematocrit, erythrocytes, and leukocytes and the protein composition of plasma were within normal ranges. Heterozygotes derived from independent ES clones were then intercrossed to determine whether mice homozygous for either mutation were viable. No mice homozygous for the Epo or EpoR null mutation were found at 3 weeks of age; since no postnatal lethality was observed, the homozygous Epo$^{-/-}$ or EpoR$^{-/-}$ mice were embryonic lethal. Examination of embryos at successive stages of embryonic development revealed that homozygous Epo$^{-/-}$ or EpoR$^{-/-}$ embryos died between days 13 and 15 of gestation. No difference was seen in mice derived from different ES clones or under different genetic backgrounds.

Example 4
Construction of Human/Murine Chimeric EPOR Target Vector

The following describes the preparation of a plasmid vector containing a DNA construct for a functional murine EPOR transgene, encoding murine introns and Exons I, VI and VII and human Exons II, III, IV and V of the EPO-receptor gene.

An 8.3 Kb SalI-XbaI fragment was isolated from a urine EPOR genomic clone, prepared as in Example 2, and subcloned into the ClaI and XbaI sites of pBluescript SK(+) cloning vector (Stratagene, La Jolla, C) to give the plasmid pBluescript.mEPOR.Sal-Xba. A 2 Kb NarI-XbaI fragment, encompassing exons II, III, IV, V and VI and the attendant introns of the murine EpoR gene, was isolated from the plasmid and subcloned into the ClaI and XbaI sites of pBluescript SK(+) to give pBluescript.mEPOR.Nar-Xba.

The CDNA of exons from human EPO receptor was amplified using the following PCR primers:

Exon II:
forward primer:
5'-cgccatggctatcccctttctagCGGCCTTGCTGGCG
GCCCCGGG (SEQ ID NO: 1),
reverse primer:
5'-ggccacccagtcctgaggactcacTCGAGCTGGTAG
GAGAGCTG (SEQ ID NO: 2);

Exon III:
forward primer:
5'-ttcttggttcccccgatcgcacagGGATGAGCCATGG
AAGCTGTG (SEQ ID NO: 3),
reverse primer:
5'-tcgctcccatcccctctcacctacCTACTTCATTGAT
GTGGATGA (SEQ ID NO: 4);

Exon IV:
forward primer:
5'-caggatccatttcactttctgcagTGCTCCTAGACGC
CCCCGTGG (SEQ ID NO: 5),
reverse primer:
5'-tgcggctgttctcttagctctcacCCTCTGTACGCTC
CCTGCGCC (SEQ ID NO: 6); and Exon V:
forward primer:
5'-tctcctggctccacccgcccccagGTGGAGATCCTG
GAGGGCCGC (SEQ ID NO: 7),
reverse primer:
5'-caccccgaggaactagggcctcacCGCTAGGCGTC
AGCAGCGACA (SEQ ID NO: 8)

to generate cDNA segments for the exons with a 24-base 5'-end (lower case) corresponding to murine intron sequence. The amplified cDNA was then purified by agarose gel electrophoresis to serve as mutagenesis primers in a "sticky feet" mutagenesis reaction.

Phagemid particles of the plasmid pBluescript.mEPOR.Nar-Xba were grown in *E. coli* CJ236.

Single-stranded mutagenesis templates were obtained and annealed in a single reaction mixture with all the mutagenesis primers and an additional single-stranded primer: 5'-CTCGAGGTCGACGGTGGCGCCACTTTTGCA AGACC (SEQ ID NO: 9), designed to recreate the NarI site destroyed when the NarI-XbaI fragment was cloned into the ClaI site of the pBluescript SK(+). The primers then were extended around the template and ligated. The resulting double-stranded DNA was transformed into *E. Coli* XL-1 and clones containing the mutations were identified by restriction mapping of DNA minipreparations, followed by DNA sequencing. one clone (#16) so isolated contained intact human exons II and II and the recreated NarI site. A second clone (#37) contained intact human exon IV and a third clone (#1) contained intact human exon V.

The final chimeric fragment was constructed by a 3-way ligation of a ClaI-BGlII fragment containing human exon IV (obtained from clone #37), a BglII-XbaI fragment containing human exon V and murine exon VI (obtained from clone #1) and a ClaI-XbI fragment containing human exons II and III and the reconstructed NarI site (obtained from clone #16). The chimeric NarI-XbaI fragment then was subcloned into the plasmid pBluescript.mEPOR.Sal-Xba, replacing the murine NarI-baI fragment with its chimeric analog, to give the plasmid pBluescript.chEPOR.Sal-Xba.

Example 5
Generation of Committed Erythroid BFU-E and CFU-E Progenitors Does Not Require EPO or EPOR Committed erythroid progenitor cells that specifically-respond to EPO are detected by the formation of discrete erythroid colonies following in vitro culture in plasma clots or methylcellulose and are termed the. colony-forming unit-erythroid (CFU-E) and the burst-forming unit-erythroid (BFU-E) (Gregory and Eaves, 1977; Gregory and Eaves, 1978). As demonstrated by thymidine suicide experiments, the CFU-E is a rapid diving cell that is highly responsive to low concentrations of EPO and gives rise to erythroblast colonies of 8–49 cells in 7 days (human) or of 8–64 cells in 2 days (mouse). The BFU-E is a more immature cell that divides less frequently. This cell requires EPO as well as other growth factors (Emerson et al., 1985), such as interleukin-3 (IL-3), granulocyte/macrophage colony-stimulating factor (GM-CSF), and stem cell factor (SCF) to develop into grouped clusters of erythroblasts or larger colonies (bursts) of greater than 500 erythroblasts by 15 days (human) or 7–10 days (mouse) in culture (Gregory and Eaves, 1977, 1978). Development from the earliest BFU-E to the latest CFU-E is a continuous process, with an intermediate progenitor often termed the mature BFU-E (Gregory and Eaves, 1977, 1978). The sensitivity of the progenitors to EPO is transient. Beyond the late basophilic erythroblast stage, the level of the EPOR drops, and the cells are no longer dependent on EPO for continued maturation (Koury and Bondurant, 1988). While EPO is thought to be required for proliferation from BFU-E to CFU-E and subsequent proliferation of the CFU-Es, the role of EPO in regulating erythroid differentiation is less defined.

Several aspects of the in vivo function of EPO and the EPOR were investigated. Specifically, whether maternal EPO can support fetal erythropoiesis; whether EPO plays a similar role in primitive and definitive erythropoiesis; whether EPO is an essential factor in determining the commitment of cells to the erythroid lineage; and whether EPO is crucial for proliferation and differentiation of some or all types of erythroid progenitor cells were investigated. To address these questions, the mouse strains carrying null mutations in the Epo or EpoR genes by gene targeting in embryonic stem cells described in Examples 1 and 2 were used. It is shown that heterozygous mice lacking one allele of the Epo or EpoR genes are viable and fertile and have normal erythrocytes and leukocytes. Homozygous mice, however, die by embryonic days 13–15 (E13–E15) with severe anemia. By culturing fetal livers from both types of homozygous embryos, it was shown that BFU-E and CFU-E progenitors were present. Thus, neither EPO nor the EPOR is required for erythroid lineage commitment or for the proliferation and differentiation of BFU-E to CFU-E progenitors. The results reveal an essential role for EPO in regulating definitive erythropoiesis by controlling processes such as proliferation, survival, and irreversible terminal differentiation of the late progenitors (CFU-E).

Methods and Materials
Histological Analysis of Embryos

Embryos were dissected free of uterine muscle and decidua, and the placenta and yolk sac were saved for genotyping. For histology, the embryos were paced in 10% buffered formalin for 24–48 hours and then in successive ethanol and xylene baths and finally embedded in Paraplast Plus (Oxford) with an Autotechnicon mono-embedder (Technicon). Embryos were sectioned by using a Reichert-Jung microtome and stained with hematoxylin and eosin.
Progenitor Cell Assays Individual fetal livers were dissected free in Iscove's modified Dulbecco's medium (IMDM), disaggregated into single cell suspensions, passed through a Cell Strainer (70 $\mu$m, Falcon), and then washed three times in IMDM medium. Cells were diluted 1:20 in 2% acetic acid to lyse nonnucleated mature erythrocytes, and then the remaining cells were counted. Cells from each fetal liver were placed in triplicate in $\alpha$-methylcellulose without growth factor or supplemented with EPO (3U/ml) or a cocktail of growth factors (3U/ml EPO and 1% pokeweed mitogen-stimulated murine spleen cell conditioned medium) (Stam-Cell Technologies, Incorporated). Colony formation was monitored at appropriate times (2–3 days for CFU-E an 7–10 days for BFU-E), and benzidine-positive colonies were counted. For retroviral infection, fetal liver cells were resuspended in medium containing a recombinant spleen focus-forming virus expressing EpoR (SFFVEpoR) (Pharr, et al., 1993) 4 $\mu$g/ml Polybrene and kept on ice for 2–3 hours. Following infection, cells were washed once and placed in $\alpha$-methycellulose as described above.
Treatment of Mice with mEPO Pregnant Epo$^{-/-}$ females, 6–8 weeks old, were injected subcutaneously every day for a total of 8 days with 3,000 U/kg mEPO (in phosphate-buffered saline containing 0.025% bovine serum albumin, provided by Amgen, Incorporated). Blood for hematocrit determinations was collected directly into hematocrit tubes (Baxter) from the retroorbital sinus under anesthesia. Baseline hematocrit determinations were performed prior to the first injection.

Results
Definitive Erythropoiesis in EpoR$^{-/-}$ or EpoR$^{-/-}$ Fetal Liver is Completely Impaired Gross examination of mutant embryos revealed that the most dramatic consequence of the Epo and EpoR mutations were severe anemia. No significant differences were observed between wild-type and heterozygous littermates. Homozygous embryos (Epo$^{-/-}$; EpoR$^{-/-}$), however, developed normally until day 13 but appeared very pale; no red coloring characteristic of the normal fetal liver could be seen in the Epo$^{-/-}$ or EpoR$^{-/-}$ embryos. Placentas surrounding the homozygous embryos were of normal size but had fewer erythrocytes. Fetal livers were four to five times smaller than those in the normal littermates and were very pale, indicating a significant reduction in erythrocyte production.

Histological examination of fetal liver sections obtained from wild-type and homozygous mutants allowed the evaluation and comparison of erythropoietic foci within the liver parenchyma. Erythropoietic islands were numerous in the livers from wild-type or heterozygous animals but were not identifiable in livers from Epo$^{-/-}$ embryos. In the wild-type or heterozygous fetal livers, erythroid cells at all stages of differentiation could be seen. In contrast, the only erythroid cells seen in the homozygous fetal livers were large erythroblasts. All liver sections also showed yolk sac derived erythrocytes with characteristic abundant eosinophilic cytoplasm and large nuclei. Many pycnotic nuclei, characteristic of apoptotic cells, were seen in liver sections from the Epo$^{-/-}$ embryos, but few were visible in fetal livers from wild-type and Epo$^{-/-}$ embryos. Confirming these results, cytospin preparations from livers of normal and homozygous mice were analyzed by Giemsa staining. Erythropoietic cells at all stages of differentiation, including many fetal liver-derived nonnucleated erythrocytes (N) and few yolk sac-derived nucleated erythrocytes (Y), were seen in the wild-type liver preparation, while only proerythroblasts (E) and yolk sac-derived nucleated erythrocytes were identifiable in the preparation from the Epo$^{-/-}$ homozygotes. The same results were obtained by analyzing the fetal livers from the Epo$^{-/-}$ embryos, compared with those from the heterozygous and wild-type embryos. These results indicate that EPO and EPOR are essential for controlling production of definitive erythrocytes in fetal liver.

Fetal Livers from Epo$^{-/-}$ Embryos Have BFU-E and CFU-E Progenitors

To determine at which stage of erythropoiesis EPO plays a crucial role, erythroid progenitors in fetal livers from Epo$^{-/-}$ embryos were quantified. Consistent with the anatomical and histological analyses, livers from Epo$^{-/-}$ fetuses had significantly decreased numbers of nucleated cells; an approximately 6-fold and 17-fold reduction at E12.5 and E13.5, respectively, compared with wild-type and heterozygous littermates.

If the Epo$^{-/-}$ fetal livers do contain CFU-Es and BFU-Es, benzidine-positive colonies after 2–3 days (for CFU-E) or 7–10 days (for BFU-E) of cultivation when exogenous EPO is supplemented should be detected, since these progenitors express the EPOR on their surface. For this purpose, single cell suspensions were prepared and plated in methylcellulose culture supplemented with a cocktail of growth factors including EPO, and benzidine-positive colonies were counted. Fetal livers from EPO$^{-/-}$ embryos contained erythroid progenitors, and the relative number of both CFU-E and BFU-E progenitors per 10$^5$ nucleated cells was significantly increased over that in the wild-type and heterozygous fetal livers. These results suggested that the homozygous fetal livers were enriched in progenitor cells. Cytospin preparations of cloned BFU-Es showed only adult-type definitive erythroid cells. The numbers of CFU-granulocyte/macrophage and CFU-megakaryocyte in cultures from homozygous Epo$^{-/-}$ fetal livers were normal, suggesting that the function of EPO in vivo is restricted to the erythroid lineage. Interestingly, in the control fetal livers, progenitor cells undergo rapid proliferation and differentiation to generate more mature forms of erythroid cells, and the number of nucleated cells per fetal liver increased 4-fold from E12.5 to E13.5. On the other hand, the relative number of progenitors decreases with embryonic development; a 3-fold and a 2-fold reduction in the numbers of CFU-E and BFU-E per 10$^5$ nucleated cells, respectively, were observed. In contrast, no significant increase in the number of nucleated cells was observed in livers from Epo$^{-/-}$ embryos, suggesting that, in the absence of EPO, fetal liver cells either become growth-arrested or undergo apoptosis. Interestingly, the number of BFU-E progenitors in homozygous fetal livers stayed constant from E12.5 to E13.5, while the number of CFU-Es decreased almost 2-fold, indicating that in the absence of EPO some of the CFU-Es underwent apoptosis, as suggested by the histologic analysis. No differences were seen in either the size or the degree of hemoglobinization among erythroid colonies derived from the Epo$^{-/-}$ homozygotes or their wild-type or heterozygous littermates.

Maternal EPO Cannot Support Fetal Erythropoiesis

It has been suggested that maternal EPO could cross the placental barrier and support fetal erythropoiesis (Koury et al., 1988). In particular, in the EPO$^{-/-}$ embryos the amount might be sufficient to allow generation of BFU-Es and CFU-Es in the fetal liver yet insufficient to support CFU-E differentiation. However, higher concentrations of EPO (3 U/ml) are required for in vitro differentiation of the earlier BFU-Es than for the later CFU-Es (0.03 U/ml) (Gregory and Eaves, 1978). The facts that Epo$^{-/-}$ embryos died at E13-E15 gestation stages, right after the switch from primitive to definitive erythropoiesis, and that no differences were seen between Epo$^{-/-}$ and Epo$^{-/-}$ mice, also suggested that maternal sources of EPO cannot substantially affect the definitive erythropoiesis in either Epo$^{-/-}$ or wild-type embryos.

To confirm that material EPO did not affect fetal erythropoiesis, Epo$^{-/-}$ heterozygous females, 0–7 days after detection of the vaginal plug, were injected daily with 3000 U/kg recombinant murine EPO (mEPO). An approximately 20% increase in hematocrit was detected in these females after 8 days of injection. However, no Epo$^{-/-}$ homozygotes were found in 83 embryos examined after E15 of gestation, and no improvement in erythropoiesis was observed in the homozygous embryos at E12–E13 gestation stages. These results strongly suggest that maternal EPO cannot support fetal erythropoiesis and that the development of BFU-E and CFU-E progenitors in the Epo$^{-/-}$ fetal liver is not due to maternal EPO.

EpoR$^{-/-}$ Fetal Livers Also Have BFU-E and CFU-E Progenitors

Definitive evidence that neither EPO nor the EPOR is required for the generation of BFU-E and CFU-E progenitors came from an analysis of homozygous EpoR$^{-/-}$ embryos. Direct detection of CFU-Es and BFU-Es in fetal livers from the Epo$^{-/-}$ embryos should not be possible by culture in methylcellulose, since EPO, acting through the EPOR, is essential for the production of both types of colonies. Indeed, when fetal liver cells from EpoR'- embryos were cultured with EPO, no CFU-Es or BFU-Es could be seen. Low levels of CFU-Es and BFU-Es, however, were detected when cultures were supplemented with a cocktail of growth factors including EPO. Therefore, fetal liver cells from E12.5 EpoR$^{-/-}$ embryos with a recombinant retrovirus expressing the wild-type EpoR (Pharr et al., 1993) were infected, and the cells were subsequently placed in methylcellulose culture without added growth factors or were supplemented with a cocktail of growth factors including EPO. In the absence of added growth factors, no CFU-Es and BFU-Es were detected after retroviral infection. In the presence of the cocktail of growth factors, the number of erythroid progenitors per 105 nucleated cells was about the same as that in normal fetal livers. Since Epo$^{-/-}$ and EpoR$^{-/-}$ embryos died at the same developmental stage and their fetal livers contained similar numbers of nucleated cells, it was assumed that the total number of progenitor cells in EpoR$^{-/-}$ fetal livers is very similar to that in Epo$^{-/-}$ fetal livers. on this basis, the infection efficiencies for BFU-E and CFU-E progenitor cells were estimated to be 40% and 53%, respectively. Thus, the generation of BFU-E and CFU-E progenitors in mouse fetal liver proceeds independently of the production and expression of EPO or EPOR, and the essential function EPO and EPOR in vivo is to enable the CFU-E progenitors to survive and to trigger their proliferation and then irreversible terminal differentiation.

Primitive Erythropoiesis in the EPO$^{-/-}$ and EPOR$^{-/-}$ Yolk Sac is Partially Impaired In early embryogenesis (E7–E11), the yolk sac is the first site of erythropoiesis. By E12, however, the major site of erythropoiesis has shifted from the yolk sac to the liver. The fact that EPO$^{-/-}$ and EPOR$^{-/-}$ mutants developed normally and survived to E13 suggested that primitive erythropoiesis at the yolk sac stage might be normal. However, both EPO$^{-/-}$ and EPOR$^{-/-}$ embryos at E10–E11 of gestation were very pale, allowing unequivocal identification of homozygous mutants. Blood vessels in the yolk sac of EPO$^{-/-}$ embryos had many fewer erythrocytes than did the normal embryos. Peripheral blood was collected from phenotypically normal and homozygous EPO$^{-/-}$ or EPOR$^{-/-}$ embryos at E11–E12 of gestation, and total blood cells were counted. There was a 5- to 10-fold reduction in the number of blood cells in either EPO$^{-/-}$ or EPOR$^{-/-}$ mutants as compared with that in wild-type or heterozygous littermates. Importantly, some primitive erythrocytes were present in the yolk sac surrounding the EPO$^{-/-}$ and EPO$^{-/-}$ embryos, through many fewer than in normal embryos. Thus, a low level of EPO and EPOR-independent erythropoiesis in the yolk sac allows homozygous EPO$^{-/-}$ and EPOR$^{-/-}$ embryos to develop and survive from E7 to E13 of gestation.

Discussion

In this study, mouse strains in which either the endogenous EPO or the EPOR gene was inactivated via homologous recombination in ES cells were generated. The results reveal a pivotal role for EPO and EPOR in erythropoiesis. Yolk sac hematopoiesis is significantly reduced and leads to severe anemia. Definitive erythropoiesis, which begins in the fetal liver and thereafter in the spleen and bone marrow of adults, is completely impaired, resulting in embryonic lethality by E13–E15. The deficiency in erythropoiesis is not at the stem cell or progenitor cell level, since both BFU-E and CFU-E progenitors are present in the fetal livers derived from both EPO$^{-/-}$ and EPOR$^{-/-}$ mice. The data indicate that the major function of EPO is to trigger proliferation and then irreversible terminal differentiation of the committed late erythroid CFU-E progenitors. EPO may also act to prevent apoptosis of CFU-Es.

EPO Does not Cross the Placenta Into the Fetus

Whether a maternal source of EPO can support fetal erythropoiesis is controversial. In sheep and monkeys, administration of EPO to pregnant females causes significant increase in the level of circulating maternal EPO and in maternal erythropoiesis (Zanjani, et al., 1993). However, there was no increase in the level of the fetal plasma EPO or in fetal eticulocyte production unless EPO was directly injected into the fetus, suggesting that the fetal rerythrocyte production is not effected by maternal levels of EPO (Zanjani, et al., 1993). The study using mice demonstrated the transfer of maternally administered [$^{125}$] EPO into the fetus (Koury, et al., 1988). Although the small size of the mouse fetus and the short gestation period in mice did not permit direct assessment of the physiological significance of transplacental transfer of EPO, this finding raises the possibility that EPO from a maternal source may be involved in the regulation of erythropoiesis in the fetus.

This question was directly addressed here in the study of EPO$^{-/-}$ and EPOR$^{-/-}$ mice. If significant amounts of maternal EPO do cross the placenta into the fetus, it is expected that EPO$^{-/-}$ mice will survive until birth. If maternal EPO cannot support fetal erythropoiesis, then EPO$^{-/-}$ mice, like EPOR$^{-/-}$ mice, should die during embryogenesis. No EPO$^{-/-}$ and EPOR$^{-/-}$ homozygous mice survived to birth, and both EPO$^{-/-}$ and EPOR$^{-/-}$ mice died at the same period of gestation with severe anemia. Administration of high doses of rEPO to pregnant EPO$^{+/-}$ females significantly increased the hematocrit of the mothers but had no effect on the erythropoiesis in the livers of EPO$^{-/-}$ fetuses or on the survival of the homozygous embryos. Thus, the results provide definitive physiological and functional evidence that, in mice, maternal EPO cannot cross the placenta and regulate fetal erythropoiesis.

The Roles of EPO and the EPOR in Primitive and Definitive Erythropoiesis

In the developing mouse embryos, the yolk sac is the original site of hematopoiesis, with the first stem cell colony-forming units (CFU-S) appearing at approximately E7 of gestation (Moore and Metcalf, 1970). By E12, the fetal liver becomes the major hematopoietic center. Fetal liver erythropoiesis and yolk sac erythropoiesis are distinct in several ways. In the blood islands of the yolk sac, erythrocytes mature as a cohort in a somewhat asynchronous fashion, which is quite different from the synchronous differentiation that occurs in the fetal liver (Tavassoli and Yoffey, 1983). Yolk sac erythropoiesis normally generates only large nucleated erythrocytes that synthesize embryonic hemoglobin. Fetal liver erythropoiesis, in contrast, produces nonnucleated erythrocytes that express adult hemoglobin. Some experiments have demonstrated that the fetal liver and yolk sac erythropoiesis differ in their responsiveness to EPO (Cole and Paul, 1966).

In EPO$^{-/-}$ and EPOR$^{-/-}$ embryos, definitive erythropoiesis was completely blocked, suggesting that EPO plays a critical role in regulating the erythrocyte production in the fetal liver. Primitive erythropoiesis in the yolk sac was, however, only partially impaired, with a 5- to 10-fold reduction in erythrocyte production. A small number of primitive erythrocytes are produced in the complete absence of either EPO or the EPOR, indicating that some of the erythroid progenitor cells in the yolk sac are able to proliferate and differentiate independent of either EPO or EPOR. Thus, the low level of CFU-E and BFU-E colonies detected in the EPOR$^{-/-}$ fetal liver prior to retroviral infection could be due to this small group of yolk sac-derived erythroid progenitors that migrated to the fetal liver after the blood circulation started at E9 of gestation. These results are not likely to be due to the leakiness of the knock-out mutations, since functional proteins are not likely to be generated from the mutant alleles. On the other hand, the results raise the very interesting possibility that two distinct populations of erythroid progenitors are present in the murine yolk sac, one being EPO- and EPOR-dependent and the other EPO- and EPOR-independent.

EPO and EPOR Are Not Required for the Formation of Definitive Erythroid Proqenitor Cells The control of erythropoiesis by EPO has been intensively studied both in vivo and in cell culture. Experimental manipulation of EPO levels in animals, either through the induction of anemia that stimulates the endogenous EPO production and increases circulating levels of erythrocytes, or through direct administration of EPO, resulted in a significant change in the number of CFU-Es, but only small nd variable effects in the number of BFU-Es in the bone marrow (Hara and Ogawa, 1977; Peschle, et al., 1979). These studies suggest that EPO induces the formation of CFU-Es from BFU-E progenitors. Administration of large amounts of EPO in humans led to a significant increase in the number of BFU-Es in the bone marrow and in the percentage of the BFU-Es active in DNA synthesis (Dessypris, et al., 1988). Whether these effects were due to a direct action of EPO to stimulate the development of BFU-Es and CFU-Es from earlier progenitors or, alternatively, to support their survival is unknown. In addition, the effects of EPO may be indirect, possibly through the stimulation of production of other hematopoietic growth acts or through nonspecific stimulation of accessory or stromal cells.

The formation of BFU-Es in cell cultures is affected by a number of growth factors besides EPO, including SCF, IL-3, and GM-CSF (Emerson, et al., 1985). It is not known how these facts function cooperatively with EPO in vivo in controlling proliferation and differentiation of erythroid progenitors. The level of EPO responsiveness correlates well with the amount of EPOR expressed on the surface of the progenitor cells. The human early BFU-Es have little or no EPOR on their surface and are not responsive to EPO. After 48–72 hours of growth in the presence of IL-3, GM-CSF, or SCF, mature (also called late) BFU-Es develop; they express low levels of EPOR and are weakly responsive to EPO (Sawada, et al., 1988, 1990). After another 4–5 days in culture, these cells give rise to a number of CFU-Es that are highly responsive to EPO (Gregory and Eaves, 1977) and express approximately 1000 EPORs on their surface (Sawada, et al., 1988). On the basis of these experiments, EPO was thought to function with other growth factors, such as IL-3, GM-CS, and SCF, in controlling the proliferation and differentiation of BFU-E progenitors to CFU-Es. EPO is clearly the crucial growth factor for the subsequent proliferation and differentiation of CFU-ES.

Molecular genetic analysis of mice with a null mutation in the gene encoding GM-CSF has indicated that GM-CSF is not crucial for erythropoiesis, or that other factors can compensate for its function (Dranoff, et al., 1994). SCF, however, is crucial for the development of BFU-E progenitor cells to the CFU-E stage, since mice lacking SCF (SI mutants) or its receptor KIT (W mutants) exhibit a significant reduction of CFU-E progenitors in their fetal liver and suffer from severe anemia (Nocka, et al., 1989). Since the survival and proliferation of the CFU-E progenitors depends absolutely on EPO, these results suggest that the committed erythroid progenitors cannot proliferate or mature further unless both the KIT and the EPOR signal transduction pathways are functional. While KIT binds several intracellular signal transduction proteins, such as P13K and PL$\gamma$C1, it is not known how it contributes to proliferation and differentiation of the erythroid cells.

Recently, it was demonstrated (Wu, et al., 1995) that SCF could replace EPO in supporting the growth and survival of HCD57 cells, an EPO-dependent erythroid cell line. Interestingly, SCF supported he proliferation of 32D cells expressing KIT only if they also expressed EPOR. In HCD57 cells, KIT and the EPOR were complexed together, and SCF rapidly induced tyrosine phosphorylation of the EPOR. These results suggested that KIT may activate the EPO/EPOR signal transduction pathway via tyrosine phosphorylation of the EPOR and, in turn, the activated EPOR could induce the further proliferation and maturation of committed erythroid progenitor cells. Fetal livers from EPOR$^{-/-}$ embryos contain CFU-Es and can be rescued by expression of recombinant EPOR, suggesting that interaction of the KIT and EPOR at or around the CFU-E stage may be particularly important for triggering subsequent cell proliferation, differentiation, or both.

In summary, it has been shown that in the absence of EPO or EPOR, BFU-E and CFU-E progenitors developed normally 30 in vivo but failed to undergo terminal differentiation to form mature erythrocytes. These results suggest that neither EPO nor the EPOR is required for erythroid lineage commitment or for the proliferation and differentiation of BFU-E to CFU-E progenitors. EPO and the EPOR are crucial in vivo for proliferation of CFU-E progenitors and their survival and irreversible terminal differentiation into erythrocytes. The results also indicate that there are no other ligands or receptors that can replace EPO and the EPOR in controlling definitive erythropoiesis. However, low levels of EPO- and EPOR-independent erythropoiesis do occur in primitive erythropoiesis at the yolk sac stage, suggesting that other mechanisms may play a critical role.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A DNA construct comprising: a) the 2.5 Kb PstI—PstI fragment of the 5' end of the mouse erythropoietin gene, b) DNA encoding a selectable marker, and c) the 5.0 Kb HindIII-KpnI fragment of the mouse erythropoietin gene, wherein the DNA encoding the selectable marker is positioned between the fragment of a) and the fragment of c).

2. A DNA construct comprising: a) the 4 Kb SalI-BamHI fragment derived from the 5' end of the mouse erythropoietin receptor gene, b) DNA encoding a selectable marker and c) the 2.7 Kb XbaI-EcoRI fragment derived from the 3' end of the mouse erythropoietin receptor gene, wherein the DNA encoding the selectable marker is positioned between the fragment of a) and the fragment of c).

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 46 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:1:

CGCCATGGCT ATCCCCTTTT CTAGCGGCCT TGCTGGCGGC CCCGGG                46

(2) INFORMATION FOR SEQ ID NO:2:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:2:

GGCCACCCAG TCCTGAGGAC TCACTCGAGC TGGTAGGAGA GCTG                  44

(2) INFORMATION FOR SEQ ID NO:3:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

TTCTTGGTTC CCCCGATCGC ACAGGGATGA GCCATGGAAG CTGTG                 45

(2) INFORMATION FOR SEQ ID NO:4:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

TCGCTCCCAT CCCCTCTCAC CTACCTACTT CATTGATGTG GATGA                 45

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

CAGGATCCAT TTCACTTTCT GCAGTGCTCC TAGACGCCCC CGTGG                 45

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

TGCGGCTGTT CTCTTAGCTC TCACCCTCTG TACGCTCCCT GCGCC                 45

(2) INFORMATION FOR SEQ ID NO:7:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

TCTCCTGGCT CCACCCGCCC CCAGGTGGAG ATCCTGGAGG GCCGC      45

(2) INFORMATION FOR SEQ ID NO:8:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CACCCCGAGG AACTAGGGCC TCACCGCTAG GCGTCAGCAG CGACA      45

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

CTCGAGGTCG ACGGTGGCGC CACTTTTGCA AGACC      35